United States Patent [19]

Lambert et al.

[11] Patent Number: 4,554,292

[45] Date of Patent: Nov. 19, 1985

[54] PROCESS FOR THE PRODUCTION OF HYDROCARBONS

[75] Inventors: Jean C. Lambert; Guy Barré; Pierre Dejaifve; Gérard Bidan, all of Grand-Couronne, France

[73] Assignee: Shell Oil Company, Houston, Tex.

[21] Appl. No.: 708,831

[22] Filed: Mar. 6, 1985

[30] Foreign Application Priority Data

Mar. 22, 1984 [FR] France .................. 84 04455

[51] Int. Cl.$^4$ .............................................. C07L 1/04
[52] U.S. Cl. .................................................. 518/728
[58] Field of Search ........................................ 518/728

[56] References Cited

U.S. PATENT DOCUMENTS 2,279,198  4/1942  Huppke ................................ 196/50

OTHER PUBLICATIONS

Pichler and Ziesecke, Brennstoff Chemie, Nr. ¾, 30 (1949), pp. 60–68.

*Primary Examiner*—Howard T. Mars

[57] ABSTRACT

Process for the production of hydrocarbons from synthesis gas in which the gas is contacted at elevated pressure and temperature over a catalyst comprising thorium oxide and zinc oxide promoted with at least one alkali metal compound. Preferably the alkali metal compound is potassium oxide. A major part of the product consists of $C_5+$-hydrocarbons.

9 Claims, No Drawings

PROCESS FOR THE PRODUCTION OF HYDROCARBONS

FIELD OF THE INVENTION

This invention relates to a process for the production of hydrocarbons from synthesis gas.

SUMMARY OF THE INVENTION

The invention relates to a process for the production of hydrocarbons from synthesis gas, which process comprises contacting the synthesis gas at elevated pressure and temperature with a catalyst comprising thorium oxide and zinc oxide promoted with at least one alkali metal compound. The catalyst may be supported on a suitable carrier such as alumina or silica. The weight ratio between $ThO_2$ and $ZnO$ in the catalyst is preferably in the range from about 0.03 to about 300. The selectivity to $C_5^+$-hydrocarbons is enhanced.

DESCRIPTION OF THE PREFERRED EMBODIMENTS

In the process according to the invention the starting material is synthesis gas, i.e. a gaseous mixture consisting substantially of $H_2$ and CO. Such $H_2/CO$ mixtures can very suitably be prepared by steam gasification or partial combustion of a carbon-containing material. Examples of such materials are wood, peat, brown coal, bituminous coal, anthracite, coke, crude mineral oil and fractions thereof as well as tars and oils extracted from tar sand and bituminous shale. The steam gasification or partial combustion is preferably carried out at a temperature of about 900°–1600° C. and a pressure of about 10–100 bar. In the process according to the invention it is advantageous to start from an $H_2/CO$ mixture with an $H_2/CO$ molar ratio of more than about 0.25 and less than about 6.

The intention is to convert the largest possible quantity of the CO present in the feed into hydrocarbons. To this end the $H_2/CO$ molar ratio in the feed is suitably about 1.0.

The process according to the invention can very suitably be carried out by conducting the feed in upward or downward direction through a vertically mounted reactor containing a fixed bed of the catalyst or by passing the gaseous feeds upwardly through a fluid catalyst bed. The process can also be carried out using a suspension of the catalyst or catalyst combination in a hydrocarbon oil. The process is preferably carried out under the following conditions: a temperature in the range from about 200° to about 600° C. and in particular from about 300° to about 500° C., a pressure in the range from about 0.1 to about 1000 bar and in particular from about 5 to about 500 bar and a space velocity in the range from 100 to 5000 Nl synthesis gas.$l^{-1}.h^{-1}$.

In order to improve the hydrocarbon yield of the process according to the invention a catalyst is applied having an extensive specific surface area, preferably in the range from about 0.1 to about 200 m²/g. Such a $ThO_2$ and $ZnO$ catalyst is preferably prepared in the following way:

$Th(NO_3)_4.4H_2O$ and $Zn(NO_3)_2.4H_2O$ are dissolved in water. While stirring, ammonia in gradually added to the solution until the pH of the solution is in the range from about 7 to about 10. The precipitated mixture of thorium hydroxide and zinc hydroxide is separated from the solution by filtration and washed. It is dried in air for 1 to 10 hours and it is calcined during to 1 to 24 hours in air at a temperature in the range from about 300° C. to about 1000° C.

By adding an alkali metal compound to the catalyst the selectivity for $C_5^+$-hydrocarbons is improved. The alkali metal is advantageously added by impregnation with a $K_2CO_3$ solution. Therefore, the process is carried out using a catalyst promoted with an alkali metal compound, such as an alkali metal hydroxide, nitrate or carbonate. In order to improve the activity and stability of the catalyst it is advantageously calcined before being used, suitably at a temperature in the range from about 400° to about 800° C.

Although any alkali metal compound may be used as catalyst promoter in the present process, preference is given to a potassium compound because it is readily available, cheap and it gives good results as to selectivity improvement.

The alkali metal content of the catalyst is advantageously chosen between about 0.01 and about 20% by weight, and preferably between about 0.5 and about 5% by weight.

The invention will now be illustrated with the aid of the following examples which are provided for illustration and not to be construed as limiting the invention.

EXAMPLE 1

Catalyst Preparation

A catalyst containing 76.4% wt thoria and 23.6% wt zinc oxide was prepared as follows:

522.88 g of zinc nitrate and 1104.24 g of thorium nitrate were dissolved in 4000 ml of water. The aqueous solution of nitrate is added to solution of ammonia (800 ml of ammonia diluted with 12,000 ml of water). Final pH=8.5. The precipiate was filtered and washed (4 times with 5000 ml of water each), dried in air (100 deg. C/72 hours) and calcined in air (500 deg. C/2 hours). Sieving the particles of a size between 0.4–0.6 mm were separated.

200 g of this catalyst are impregnated with an aqueous solution of potassium carbonate (3.535 g dissolved in 40 ml of water), dried in air (200 deg. C/2 hours) and calcined in air (500 deg. C/2 hours).

EXAMPLE 2

A gaseous mixture of hydrogen and carbon monoxide having a $CO/H_2$ molar ratio of 1 was passed over a bed of catalyst particles consisting of 76.4% wt $ThO_2$ and 23.6% wt $ZnO$ (as prepared according to Example 1) promoted by 1% by weight of potassium in the form of $K_2O$ and having a specific surface area of 13 m²/g which was the result of a previous calcination step carried out in air for 2 hours at 450° C.

The reaction conditions were chosen as follows:

| | |
|---|---|
| Temperature | 450° C. |
| Pressure | 80 bar abs. |
| Gas hourly space velocity | 929 Nl/l · h |

The space time yield of $C_5^+$-hydrocarbons was 61.9 g.$l^{-1}.h^{-1}$.

The liquid $C_5^+$-hydrocarbon fraction falls in the gasoline boiling range (final boiling point: 252° C.) and has a research octane number equal to 90.

COMPARATIVE EXPERIMENT 1

The experiment of Example 2 was repeated using the same conditions with the exception of the catalyst *not* containing potassium.

The space time yield of $C_5^+$-hydrocarbons was 28.7 g.l$^{-1}$.h$^{-1}$.

By comparing the results given in Example 2 with those of this comparative experiment it can be concluded that by adding an alkali metal compound to the catalyst the $C_5^+$ space time yield is increased.

COMPARATIVE EXPERIMENT 2

A gaseous mixture of hydrogen and carbon monoxide having a $CO/H_2$ molar ratio of 1 was passed over a bed of $ThO_2$ as catalyst promoted with 1% $K_2O$ and having a specific surface area of 12 m$^2$/g which had been calcined in air for 2 hours at 500° C. The catalyst particles size was from 0.4–0.6 mm.

The reaction conditions were the same as those used in Example 2.

The space time yield of $C_5^+$-hydrocarbons was 54.2 g.l$^{-1}$.h$^{-1}$.

By comparing the results given in Example 2 with those of this comparative experiment it can be concluded that a catalyst consisting of $ThO_2$ and $ZnO$ promoted with $K_2O$ shows unique properties with respect to the production of $C_5^+$-hydrocarbons.

We claim:

1. A process for the production of hydrocarbons from synthesis gas, which process comprises contacting the synthesis gas at elevated pressure and temperature with a catalyst comprising thorium oxide and zinc oxide promoted with at least one alkali metal compound.

2. The process of claim 1, wherein the catalyst has a specific surface area in the range from 0.1 to 200 m$^2$/g.

3. The process of claim 1, wherein the alkali metal compound is alkali metal oxide.

4. The process of claim 1, wherein the alkali metal compound is a potassium compound.

5. The process of claim 1, wherein the catalyst contains an alkali metal content in the range from 0.01 to 20% by weight.

6. The process of claim 1, wherein it is carried out at a pressure in the range from 0.1 to 1000 bar abs., a temperature in the range from 200° C. to 600° C. and a space velocity in the range from 100 to 5000 normal liters synthesis gas per liter of catalyst per hour.

7. The process of claim 1, wherein the synthesis gas consists substantially of $H_2$ and CO, the $H_2/CO$ molar ratio being in the range from 0.25 to 6.0.

8. The process of claim 1, wherein the weight ratio between $ThO_2$ and ZnO in the catalyst is in the range from 0.03 to 300.

9. A process for the production of hydrocarbons from synthesis gas, which process comprises contacting the synthesis gas at a temperature in the range from about 200° C. to about 600° C. and a pressure in the range between about 0.1 to about 1000 bar abs. with a catalyst comprising thorium oxide and zinc oxide promoted with at least one alkali metal compound.

* * * * *